(12) United States Patent
Tanaka et al.

(10) Patent No.: US 7,173,008 B2
(45) Date of Patent: Feb. 6, 2007

(54) LYOPHILIZED HGF PREPARATIONS

(75) Inventors: Katsumi Tanaka, Takatsuki (JP); Kanji Higashio, Kawagoe (JP); Eitaro Kumazawa, Tochigi (JP)

(73) Assignees: Toshikazu Nakamura, Kyoto (JP); Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/188,091

(22) Filed: Jul. 25, 2005

(65) Prior Publication Data

US 2006/0229245 A1    Oct. 12, 2006

Related U.S. Application Data

(63) Continuation of application No. 10/171,791, filed on Jun. 17, 2002, now abandoned, which is a continuation of application No. 08/981,846, filed as application No. PCT/JP96/01898 on May 22, 1998, now abandoned.

(30) Foreign Application Priority Data

Jul. 11, 1995    (JP)    .................................. 7-199018

(51) Int. Cl.
  *A61K 38/18*    (2006.01)
  *C07K 14/475*    (2006.01)
(52) U.S. Cl. ........................... 514/12; 514/59; 530/399
(58) Field of Classification Search .................... None
   See application file for complete search history.

(56) References Cited

U.S. PATENT DOCUMENTS

| | | | |
|---|---|---|---|
| 4,478,829 A | 10/1984 | Landaburu et al. | |
| 5,234,908 A | 8/1993 | Szabo et al. | |
| 5,510,327 A | 4/1996 | Hayasaka et al. | |
| 5,587,359 A | 12/1996 | Higashio et al. | |
| 5,736,506 A * | 4/1998 | Naka | 514/2 |
| 5,840,311 A | 11/1998 | Nakamura et al. | |
| 5,849,689 A * | 12/1998 | Chamow et al. | 514/8 |

FOREIGN PATENT DOCUMENTS

| | | |
|---|---|---|
| EP | 0308238 A1 | 3/1989 |
| EP | 0456188 A1 | 11/1991 |
| EP | 0462277 A1 | 12/1991 |
| EP | 0517182 A1 | 12/1992 |
| EP | 0722737 A | 7/1996 |
| JP | 6-40935 | 2/1994 |
| JP | 6-40938 | 2/1994 |
| JP | 6-172207 | 6/1994 |
| JP | 6-247872 | 9/1994 |
| WO | WO-95/07709 | 3/1995 |

OTHER PUBLICATIONS

Japanese language and English language translation of Tsutomu Arakawa, "How Additives Stabilize Proteins in Freezing Process", Protein, Nucleic Acid, and Enzyme, vol. 37, No. 9, pp. 1517-1523, 1992.

* cited by examiner

*Primary Examiner*—Christine J. Saoud
(74) *Attorney, Agent, or Firm*—Birch, Stewart, Kolasch & Birch, LLP

(57) ABSTRACT

The invention relates to a lyophilized HGF preparation prepared by lyophilizing an aqueous solution containing HGF, and a lyophilized HGF preparation containing a stabilizer, sodium chloride, a buffer, and/or a surface active agent. According to the invention, HGF can be stabilized, and it can be stored for a long period.

9 Claims, No Drawings

LYOPHILIZED HGF PREPARATIONS

This application is a Continuation of application Ser. No. 10/171,791 filed on Jun. 17, 2002, now abandoned, which is a Continuation of application Ser. No. 08/981,846 filed on May 22, 1998, now abandoned, which was the national phase of PCT International Application No. PCT/JP96/01898 filed on Jul. 8, 1996, which also claims priority under 35 U.S.C. § 119(a) on Patent Application No. 199018/1995 filed in Japan on Jul. 11, 1995. The entire contents of each of the above documents is hereby incorporated by reference.

TECHNICAL FIELD

The present invention relates to a lyophilized HGF preparation obtained by lyophilizing a solution containing HGF (hepatocyte growth factor). More particular, it relates to the lyophilized HGF preparation containing at least one of stabilizer, sodium chloride, buffer or surface active agent. The invention hence presents a stabilized preparation of HGF that can be stored for a long period.

BACKGROUND ART

HGF is a protein that enhances proliferation of liver parenchyma cells, and proteins having different amino acid sequences have been reported, and are known in the names of HGF, TCF, SCF, etc. In the invention, these known proteins having hepatocyte growth activity are collectively called HGF.

HGF is a physiological active peptide showing various pharmacological actions, and its pharmacological actions are reported, for example, in Experimental Medicine (Japan), Vol. 10, No. 3 (extra issue), 330–339 (1992). Owing to its pharmacological actions, HGF is expected to be developed as agent for liver cirrhosis, agent for kidney disease, epithelial cell growth promoter, carcinostatic agent, side effect inhibitor for cancer therapy, agent for lung disorder, agent for gastroduodenal lesion, agent for cerebral and nervous disorder, agent for relieving side effects caused by immunosuppressants, collagen decomposition promoter, agent for cartilage disorder, agent for arterial disease, agent for lung fibroid, agent for liver disease, agent for abnormal blood clotting, agent for hypoproteinemia, wound cure agent, improving agent for nervous disorder, hematopoietic stem cell promoter, hair growth promoter, etc. (Japanese Laid-open Patent No. 4-18028, Japanese Laid-open Patent No. 4-49246, EP No. 492614, Japanese Laid-open Patent No. 6-25010, WO 93/8821, Japanese Laid-open Patent No. 6-172207, Japanese Laid-open Patent No. 7-89869, Japanese Laid-open Patent No. 6-40934, WO 94/2165, Japanese Laid-open Patent No. 6-40935, Japanese Laid-open Patent No. 6-56692, Japanese Laid-open Patent No. 7-41429, WO 93/3061, Japanese Laid-open Patent No. 5-213721, etc.).

Preparations of HGF are disclosed in WO 90/10651 and Japanese Laid-open Patent No. 6-247872. This publication of WO 90/10651 discloses a deletion type HGF (dLeHGF) deleting five residues of amino acid from HGF, and it is named TCFII. This specification shows that HGF is stabilized by albumin, human serum, gelatin, sorbitol, mannitol, xylitol, etc. But, it relates to aqueous solution preparations, and HGF is stabilized in an aqueous solution. The publication of Japanese Laid-open Patent No. 6-247872 unveils a preparation having HGF contained at high concentration by coexistence of basic amino acids and HGF (TCF).

Generally, the protein is not so stable in freezing operation (Protein, Nucleic Acid, Enzyme (Japan), 37(9), 1517, 1992). The stabilizer of protein in an aqueous solution is intended to stabilize by mutual action of water molecule and protein. Therefore, in a lyophilized preparation of protein in the absence of water, the stabilizer of protein for an aqueous solution shows no stabilizing effect in most cases (Protein, Nucleic Acid, Enzyme (Japan), 37(9), 1517, 1992).

On the other hand, nothing has been known about lyophilized HGF preparation, and it could not expected how far the lyophilized HGF preparation would show physical and biological stability.

The aqueous solution preparation of HGF itself is, when stored at low temperature or room temperature for several days, changed in properties, showing aggregation, turbidity and gelation, and forms variants and polymers, and it is low in physical stability and is lowered in biological activity, and hence it is low in stability of biological activity and is not a stable preparation suited long-term storage. It has been a fatal point for development of HGF as medicines or animal drugs in a form of injection preparation. The invention solves the above-mentioned problems. That is, it is an object of the invention to present a stable preparation which can store for a long period as medicines for medical treatment or animal drugs.

DISCLOSURE OF THE INVENTION

The invention relates to a lyophilized HGF preparation. This lyophilized HGF preparation may contain a stabilizer such as glycine, alanine, sorbitol, mannitol, and dextran sulfate, or may contain a buffer such as citrate.

Other invention of the present invention relates to a lyophilized HGF preparation containing stabilizer, sodium chloride, buffer and surface active agent.

In the lyophilized HGF preparation of the invention, HGF is stabilized and can be stored for a long period.

THE BEST MODE FOR CARRYING OUT THE INVENTION

As HGF used in the present invention, there can be used one which prepared by various methods if it is purified to an extent that it can be used as a medicine.

Various methods are known for preparing HGF. For example, HGF can be obtained by extraction and purification from organs (e.g. liver, spleen, lung, bone marrow, brain, kidney, placenta, etc.), blood cells (e.g. platelet, leucocyte, etc.), serum and plasma of mammals such as rat, cow, horse, sheep and the like (see FEBS Letters, 224, 312, 1987; Proc. Natl. Acad. Sci. USA, 86, 5844, 1989, etc.).

Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises cloning the gene coding HGF with a proper vector, inserting it into a proper host cell to give a transformant, and separating the desired recombinant HGF from the culture supernatant of the transformant (e.g. Nature, 342, 440, 1989, Japanese Laid-open Patent No. 5-111383, Biochem. Biophys. Res. Commun., 163, 967, 1989). The host cell is not specifically limited, and various host cells conventionally used in gene engineering methods can be used, which are, for example, Escherichia coli, Bacillus subtilis, yeast, filamentous fungi, and plant or animal cells.

More specifically, the method of extracting and purifying HGF from live tissues is, for example, to administer carbon tetrachloride to a rat intraperitoneally, remove a liver from the rat with hepatitis, grind it, and purify by the ordinary protein purifying technique such as gel column chromatography using S-Sepharose and heparin Sepharose, HPLC and the like.

Further, by the gene engineering method, the gene coding the amino acid sequence of human HGF is cloned into a vector such as bovine papilloma virus DNA and the like to obtain an expression vector, and by using this expression vector, animals cells such as Chinese hamster ovary (CHO) cells, mouse C127 cells, monkey COS cells and the like are transformed, and HGF can be obtained from the culture supernatant of the transformants.

In thus obtained HGF, a part of the amino acid sequence of HGF may be deleted or substituted by other amino acid(s), another amino acid sequence may be inserted, one or more amino acids may be bonded to the N-terminal and/or C-terminal, or saccharide chain(s) may likewise be deleted or substituted, providing it has substantially the same effect as HGF.

The "lyophilized HGF preparation" refers to a preparation prepared by lyophilizing an aqueous solution containing HGF by use of an ordinary lyophilizing method.

The "stabilizer" includes amino acids (e.g. glycine, alanine, etc.), polysaccharides (e.g. heparin, dextran sulfate, etc.), sugar alcohols (e.g. sorbitol, mannitol, etc.) and the like, and two or more types thereof may be used simultaneously. The lyophilized HGF preparation prepared by adding the stabilizer is a preparation further increased in storage stability of HGF. Preferred stabilizers are glycine, alanine, sorbitol, mannitol, and dextran sulfate. For example, a preferred adding amount of glycine, alanine, sorbitol or mannitol is 0.01 to 100 times by weight of the weight of HGF, and more preferably 0.1 to 10 times by weight.

The "buffer" includes, for example, phosphate buffer and citrate buffer. The buffer acts to adjust the pH of the aqueous solution after re-dissolving, and keep the solubility of HGF. That is, for example, in the case of the recombinant HGF used in Examples, the solubility of HGF varies with the pH, and the solubility is about 0.1 to 5.0 mg/ml around pH 7, but the solubility is over 20 mg/ml around pH 5, and therefore it is preferred to keep the pH around 5.0 to 6.0. A preferred buffer is a citrate buffer, and more preferably sodium citrate buffer is used. This citrate buffer also contributes to stabilization of HGF in an aqueous solution after re-dissolving. A preferred range of adding the buffer is, for example, 1 to 100 mM to the amount of water after re-dissolving.

The "surface active agent" includes, for example, polysorbate 20, polysorbate 80, pluronic F-68, and polyethylene glycol, and two or more types thereof may be used simultaneously. A particularly preferred surface active agent is polysorbate 80. It is known that HGF is likely to be adsorbed on a container material such as glass and resin. Therefore, by adding a surface active agent, adsorption of HGF after re-dissolving to the container is prevented. A preferred range of adding amount of surface active agent is 0.001 to 2.0% by weight, for example, to the weight of water after re-dissolving.

The "sodium chloride" acts to keep solubility of HGF. That is, for example, in the case of recombinant HGF used in Examples, the solubility is enhanced by adding sodium chloride, and the solubility is notably increased in particular at 300 mM or more (Japanese Laid-open Patent No. 6-247872). An amount of addition of sodium chloride is limited by the osmotic pressure ratio, but it may be an amount showing an osmotic pressure ratio of injection preparation for general use. In particular, the osmotic pressure ratio is preferred to be 1 to 2 which is permitted as the osmotic pressure ratio of injection for medical treatment or animal drug, and it is preferred to add, for example, by 150 to 300 mM to the amount of water after re-dissolving.

The lyophilzed HGF preparation is prepared by lyophilizing an aqueous solution containing HGF by an ordinary lyophilizing method. For example, HGF is dissolved in a proper solvent (for example, sterilized water, buffer, physiological saline, etc.), filtered through a filter to be sterilized, and, if necessary, stabilizer, buffer, surface active agent, sodium chloride and others may be added, and the mixture is lyophilized. The preparation of the invention may contain additives necessary for pharmaceutical manufacturing, for example, a dissolving aid, an antioxidant, a pain-alleviating agent, an isotonic agent, and the like. The lyophilizing method may comprise three unit operations, for example, (1) a freezing step of cooling and freezing under ordinary pressure, (2) a first drying step of sublimating and drying free water not restrained by solute under reduced pressure, and (3) a second drying step of removing the intrinsic adsorbed water and crystal water of solute (Pharm. Tech. Japan, 8(1), 75–87, 1992). HGF is very stable when preparing a solution, when lyophilizing, and in an aqueous solution by re-dissolving the lyophilized preparation. The content of HGF may be properly adjusted depending on the disease to be treated and route of administration.

The lyophilized preparation is used by adding distilled water for injection and re-dissolving, before use.

INDUSTRIAL APPLICABILITY

The lyophilized HGF preparation of the invention can stabilize HGF, and can be stored for a long period.

EXAMPLES

The invention is further described by presenting Examples, but it must be noted that the invention is not limited to these Examples alone. In the Examples, dLeHGF (five-amino acid depletion type HGF, also known as TCFII) disclosed in the publication of WO 90/10651 was used.

Example 1

Preparation of Lyophilized HGF Preparation

In 10 mM citrate buffer (pH 5.0) containing 300 mM sodium chloride and 0.01% polysorbate 80, HGF was dissolved by 20 mg/ml, and an aqueous solution of HGF was obtained aseptically. After adjusting the pH of the aqueous solution, it was aseptically charged into a vial, and lyophilized in the condition as shown in Table 1, and a lyophilized HGF preparation was obtained. The arrow mark (→) in the table shows the temperature is changed.

TABLE 1

|  | Freezing step | | First drying step | | Second drying step | |
|---|---|---|---|---|---|---|
| Temperature (° C.) | 5 → −40 | −40 | −40 → 0 | 0 | 0 → 20 | 20 |
| Time (hr) | 1 | 10 | 8 | 24 | 1 | 24 |
| Pressure (mmHg) | 760 | 760 | <1 | <1 | <1 | <1 |

Example 2

Preparation of Lyophilized HGF Preparation

A lyophilized HGF preparation was obtained by using 10 mM citrate buffer (pH 6.0) instead of 10 mM citrate buffer (pH 5.0) in Example 1.

Example 3

Preparation of Lyophilized HGF Preparation

A lyophilized HGF preparation was obtained by using 10 mM phosphate buffer (pH 6.0) instead of 10 mM citrate buffer (pH 5.0) in Example 1.

Example 4

Preparation of Lyophilized HGF Preparation

A lyophilized HGF preparation was obtained by using 10 mM phosphate buffer (pH 7.0) instead of 10 mM citrate buffer (pH 5.0) in Example 1.

Example 5

Preparation of Lyophilized HGF Preparation

In 10 mM citrate buffer (pH 5) containing 300 mM sodium chloride and 0.01% polysorbate 80, HGF was dissolved by 20 mg/ml. In succession, glycine was dissolved by 50 mg/ml. and a dissolved solution of HGF was obtained aseptically. After adjusting the pH of the dissolved solution, it was aseptically charged into a vial, and lyophilized in the same condition as in Example 1 and a lyophilized HGF preparation was obtained.

Example 6

Preparation of Lyophilized HGF Preparation

A lyophilized HGF preparation was obtained by using alanine instead of glycine in Example 5.

Example 7

Preparation of Lyophilized HGF Preparation

In 10 mM citrate buffer (pH 5) containing 300 mM sodium chloride and 0.01% polysorbate 80, HGF was dissolved by 20 mg/ml. In succession, sorbitol was dissolved by 200 mg/ml, and a dissolved solution of HGF was obtained aseptically. After adjusting the pH of the dissolved solution, it was aseptically charged into a vial, and lyophilized in the same condition as in Example 1 and a lyophilized HGF preparation was obtained.

Example 8

Preparation of Lyophilized HGF Preparation

In 10 mM citrate buffer (pH 6) containing 300 mM sodium chloride and 0.01% polysorbate 80, HGF was dissolved by 10 mg/ml. In succession, dextran sulfate was dissolved by 50 mg/ml, the pH was adjusted, and a dissolved solution of HGF was obtained. It was then charged into a vial, and lyophilized in the same condition as in Example 1 and a lyophilized HGF preparation was obtained.

Example 9

Preparation of Lyophilized HGF Preparation

A lyophilized HGF preparation was obtained in the sane manner as in Example 1, except by using 10 mM citrate buffer (pH 6.0) instead of 10 mM citrate buffer (pH 5.0), and regulating HGF concentration at 10 mg/ml.

Test Example 1

Effects of Lyophilizing Process on Biological Activity of HGF

To observe changes in biological activity of HGF in the lyophilizing process, using HGF aqueous solution before lyophilization and HGF aqueous solution re-dissolved directly after lyophilization in Example 1, the biological activity of HGF was measured (the measuring method of biological activity is shown below). The results are shown in Table 2. Since the specific activity was not changed before and after lyophilization, it is shown that the biological activity of HGF is not inactivated by the lyophilizing process and re-dissolving, which suggests that HGF is usable as a lyophilized preparation.

Measuring Method of Biological Activity

Hepatocytes obtained by liver perfusion of male Wistar rats were purified, and, after confirming the cell survival rate, seeded on a plate at $1\times10^4$/well. After pre-incubation for 20 hours in 5% carbon dioxide incubator, HGF sample and standard sample were added (n=3). After further pre-incubation for 24 hours in 5% carbon dioxide incubator, [$^3$H-thymidine] was added to label for 2 hours. Cells were collected by a cell harvester, and the amount of [$^3$H] taken into cells was measured. Results of measurement were verified by a parallel line calibration method, and the specific activity to the standard sample was determined.

TABLE 2

| Biological activity before and after lyophilization | |
|---|---|
| Sample | Specific activity |
| Solution preparation before lyophilization | 0.89 |
| Lyophilized preparation immediately after re-dissolving | 0.94 |

Test Example 2

Properties After Dissolving Lyophilized Preparation

Lyophilized preparations prepared in Examples were stored for 1 month at −40° C., 25° C., and 50° C., and dissolved, and properties of the dissolved preparations were observed visually. The lyophilized preparation was dissolved by using purified water. Results are shown in Table 3. When stored at −40° C. or 25° C., the preparations of all Examples were stable in the properties. When stored at 50° C., the preparation in Example 1 was turbid immediately after dissolving, but preparations of Examples 5, 6 and 7 were stable in properties.

TABLE 3

| Properties after dissolving lyophilized preparations (stored for 1 month) | | | |
|---|---|---|---|
| | Properties | | |
| Preparation | −40° C. | 25° C. | 50° C. |
| Example 1 | Clear | Clear | Turbid |
| Example 5 | Clear | Clear | Clear |
| Example 6 | Clear | Clear | Clear |
| Example 7 | Clear | Clear | Clear |

Test Example 3

Polymer Content Changes in Lyophilized Preparations

Lyophilized preparations prepared in Examples 1, 5, 6 and 7 were stored for 1 month or 2 months at −40° C., 25° C., 40° C., and 50° C., and the ratio of polymer content and HGF content contained in the lyophilized preparations were measured. The measuring method is the gel filtration method as explained below. Results are shown in Table 4 and Table 5. Regardless of the storage temperature, a polymer production was low in the preparations of all Examples, and the preparations were stable physically. In particular, the polymer production was extremely small in the preparations of Examples 5, 6 and 7, and the preparations were stable physically.

Measuring Method of Polymer Content

The concentration of HGF Nv as diluted to 2 mg/ml, and was measured in the following conditions by the gel filtration method.
Column: TOSOH TSK G-3000SW XL (φ0.78×30 cm)
Flow velocity: 0.5 ml/min
Detection: OD 280
Temperature: 25° C.
Carrier: 10 mM Tris, 150 mM NaCl, 0.05% SDS, pH 7.0
Application: 20 μl
Retention time of polymer: 13.0 min
Retention time of HGF: 14.4 min

TABLE 4

Polymer content/HGF content in lyophilized preparations stored for 1 month

|  | −40° C. | 25° C. | 40° C. | 50° C. |
| --- | --- | --- | --- | --- |
| Example 1 | 1.07% | 1.59% | 2.76% | 6.17% |
| Example 5 | 0.92% | 1.39% | 1.83% | 4.09% |
| Example 6 | 0.93% | 1.54% | 1.81% | 2.90% |
| Example 7 | 0.90% | 1.35% | 2.57% | 6.64% |

TABLE 5

Polymer content/HGF content in lyophilized preparations stored for 2 months

|  | −40° C. | 25° C. | 40° C. | 50° C. |
| --- | --- | --- | --- | --- |
| Example 1 | 0.92% | 1.44% | 3.91% | 12.23% |
| Example 5 | 0.88% | 1.21% | 2.49% | 7.49% |
| Example 6 | 0.85% | 1.10% | 1.96% | 5.76% |

Test Example 4

Effects of Dextran Sulfate on Polymer Production

The lyophilized preparation prepared in Example 8 was stored for 1 month at 5° C., and the ratio of polymer content and HGF content contained in the lyophilized preparations were measured. The measuring method was same as in Test example 3. As a comparative example, the lyophilized preparation of Example 9 prepared in the same composition and method except that dextran sulfate was not contained was used and tested similarly. The results are shown in Table 6. As shown in Table 6, by adding dextran sulfate, it has been found that the polymer production was low even if stored at high temperature, and that the stability is enhanced.

TABLE 6

Polymer content/HGF content of lyophilized preparations

|  | Before start of storage | After storage for 1 month at 50° C. |
| --- | --- | --- |
| Example 8 | 2.46% | 9.45% |
| Example 9 | 1.78% | 14.01% |

Test Example 5

Changes of Biological Activity of Lyophilized Preparations

Lyophilized preparations prepared in Examples 1, 5, 6 and 7 were stored for 1 month or 2 months at −40° C., 40° C., 50° C. and 60° C. and the biological activity of the aqueous solution after re-dissolving the lyophilized preparations was measured by the biological activity measuring method shown in Test example 1. The results are shown in Table 7 and Table 8. The initial values of biological activity of aqueous solutions after re-dissolving the preparations in Examples 1, 5, 6 and 7 were respectively 1.01±0.25, 0.91±0.18, 0.88±0.05, and 1.03±0.04. When stored at 60° C. a slightly lowering tendency was noted in the biological activity, but when stored at 50° C. or lower temperature, there was almost no change in the biological activity in the preparations of any Example, and the biological activity was stable.

TABLE 7

Biological activity of lyophilized preparations stored for 1 month (specific activity)

|  | −40° C. | 40° C. | 50° C. | 60° C. |
| --- | --- | --- | --- | --- |
| Example 1 | 0.96 ± 0.13 | 0.92 ± 0.13 | 0.81 ± 0.07 | 0.54 ± 0.05 |
| Example 5 | 0.80 ± 0.14 | 0.99 ± 0.10 | 0.80 ± 0.16 | 0.72 ± 0.03 |
| Example 6 | 0.92 ± 0.14 | 1.02 ± 0.06 | 0.94 ± 0.08 | 0.78 ± 0.03 |
| Example 7 | 0.92 ± 0.02 | 0.97 ± 0.04 | 0.83 ± 0.06 | — |

TABLE 8

Biological activity of lyophilized preparations stored for 2 months (specific activity)

|  | −40° C. | 40° C. | 60° C. |
| --- | --- | --- | --- |
| Example 1 | 1.14 ± 0.14 | 0.98 ± 0.01 | 0.46 ± 0.09 |
| Example 5 | 0.95 ± 0.05 | 0.84 ± 0.09 | 0.57 ± 0.01 |
| Example 6 | 1.11 ± 0.14 | 1.09 ± 0.03 | 0.52 ± 0.02 |

The invention claimed is:

1. A method of producing a stabilized lyophilized hepatocyte growth factor (HGF) preparation, which comprises lyophilizing an aqueous HGF solution comprising dextran sulfate as a storage stabilizer.

2. The method of producing a stabilized lyophilized HGF preparation according to claim 1, wherein dextran sulfate is present in an amount of 0.1 to 10 times by weight of the weight of HGF.

3. The method of producing a stabilized lyophilized HGF preparation according to claim 1, wherein the aqueous HGF solution further comprises a buffer.

4. The method of producing a stabilized lyophilized HGF preparation according to claim 3, wherein the buffer is a citrate buffer.

5. The method of producing a stabilized lyophilized HGF preparation according to claim 4, wherein the citrate buffer is a sodium citrate buffer.

6. The method of producing a stabilized lyophilized HGF preparation according to claim 1, wherein the aqueous HGF solution further comprises sodium chloride, sodium citrate and a surface active agent.

7. A lyophilized aqueous composition comprising:
hepatocyte growth factor (HGF), and
dextran sulfate.

8. The lyophilized aqueous composition according to claim 7, further comprising
a buffer.

9. The lyophilized aqueous composition according to claim 7, further comprising
sodium chloride,
sodium citrate and
a surface active agent.

* * * * *